United States Patent [19]

Alguard

[11] Patent Number: 4,699,510
[45] Date of Patent: Oct. 13, 1987

[54] COLOR SENSOR

[75] Inventor: Mark J. Alguard, Palo Alto, Calif.

[73] Assignee: Measurex Corporation, Cupertino, Calif.

[21] Appl. No.: 669,110

[22] Filed: Nov. 7, 1984

[51] Int. Cl.⁴ ............... G01J 3/50; G01N 21/27; G01N 21/64
[52] U.S. Cl. ............... 356/73; 250/459.1; 250/461.1; 356/317; 356/407; 356/417
[58] Field of Search .......... 356/73, 317, 318, 407, 356/417; 250/458.1, 459.1, 461.1, 461.2

[56] References Cited

U.S. PATENT DOCUMENTS

| | | | |
|---|---|---|---|
| 3,663,813 | 5/1972 | Shaw | 250/461.1 |
| 3,944,368 | 3/1976 | Beesley | 356/30 |
| 3,973,129 | 8/1976 | Blumberg et al. | 250/461.2 |
| 4,019,819 | 4/1977 | Lodzinski | 356/73 |
| 4,100,416 | 7/1978 | Hirschfeld | 356/318 |
| 4,117,338 | 9/1978 | Adrion et al. | 250/461.1 |
| 4,421,772 | 12/1983 | Munck et al. | 356/317 |

FOREIGN PATENT DOCUMENTS 0153148  9/1983  Japan ................. 356/317

Primary Examiner—F. L. Evans
Attorney, Agent, or Firm—Spensley Horn Jubas & Lubitz

[57] ABSTRACT

An improved color sensor is provided having two sources of illumination, one source being modulated on and off while the other source remains on. Data taken while the modulated source is on is compared with data taken while the modulated source is off to compute the effective fluorescence of the sample. A corrected color spectrum can then be determined for a defined source.

16 Claims, 10 Drawing Figures

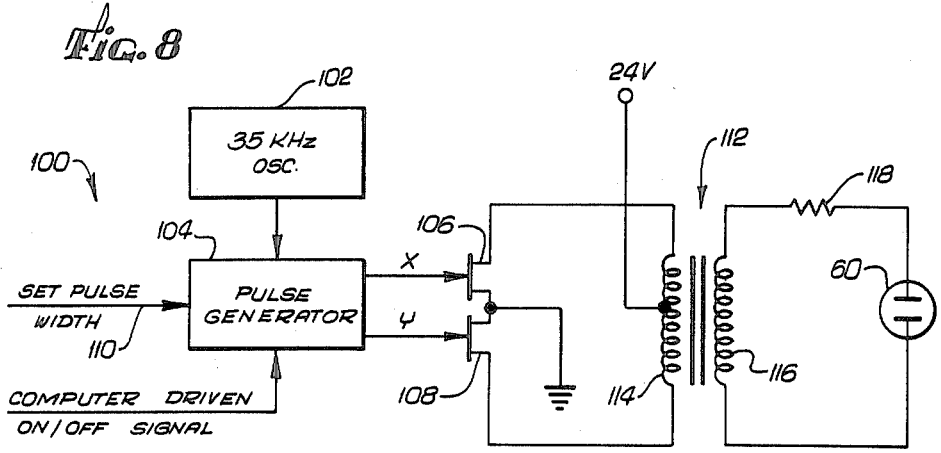
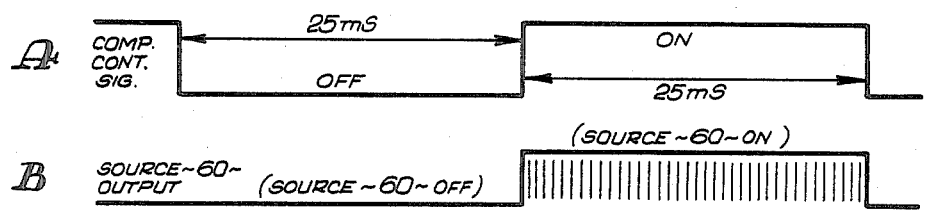
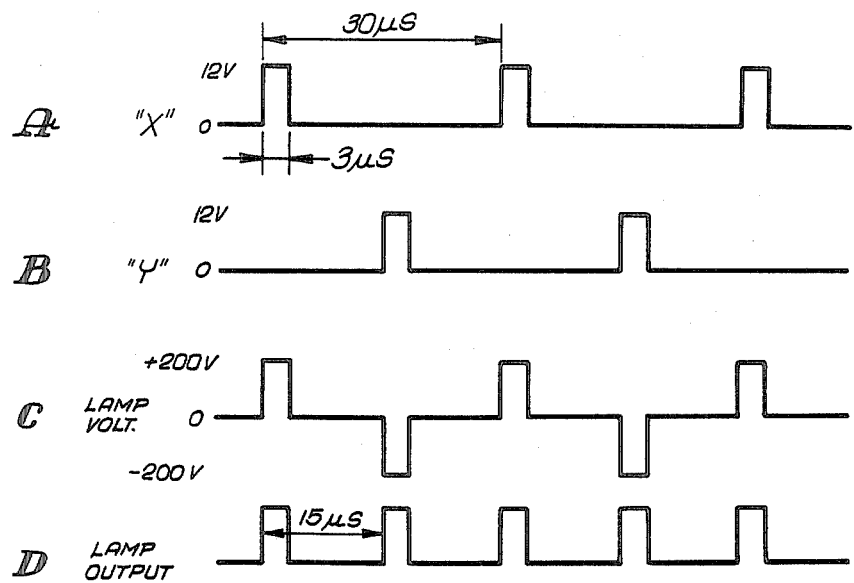

COLOR SENSOR

BACKGROUND OF THE INVENTION

1. Field of the Invention

The present invention relates to color sensors, and more particularly, to sensors for measuring the reflective and fluorescent properties of various objects such as paper.

2. Description of the Prior Art

In industry, it is often important to accurately measure the color of an object as it is being manufactured. For instance, purchasers of paper frequently require the paper color to accurately match the color of previous purchases. Thus, paper manufacturers need to measure and control the color of paper to a previously determined value.

In the absence of fluorescence, the whiteness or color of an object is in general determined by the way the object absorbs and reflects light across the visible spectrum which when defined in terms of wavelength, is approximately 380 to 780 nanometers (nm). For example, white objects reflect light evenly across the spectrum while colored objects absorb some wavelengths (or color) and reflect others.

Color sensors typically illuminate the object and measure the intensity of the reflected light at each of a number of wavelengths. Each measured intensity of reflected light can be related to a previously measured intensity of light which has been reflected from a white standard to provide a reflectance co-efficient at each wavelength. The set of reflectance co-efficients is often referred to as the color spectrum of the object.

Because paper naturally has a somewhat offwhite or straw color, fluorescent whitening agents (FWA) in the form of dyes are often added to the paper pulp to give the finished paper product a whiter appearance. Fluorescence is the phenomenon in which energy is absorbed over a range of wavelengths (the excitation band) and then reemitted in a lower energy (longer wavelength) band referred to as the emission band. Fluorescent whitening agents typically absorb the violet and ultraviolet energies and remit this energy in the blue range to give the paper a whiter appearance.

The degree to which the object or paper illuminated by a particular source is made to appear bluer (or whiter) by the FWA depends upon the proportion of the energy emitted by the source in the violet and ultraviolet regions as compared to the blue and other lower energy spectra, and also upon the effective concentration level of the fluorescent agent. Thus, if the excitation emission spectrum of the source changes, the amount of fluorescence and hence the color of the object will change. The emission spectra of various standard sources have been defined by the Commission Internationale de L'Eclairage (CIE) but attempts to build standard sources which exactly duplicate the defined spectra have been largely unsuccessful. As a result, the emission spectra of the sources used in color sensors usually varies from sensor to sensor so that measured color spectra for a given fluorescent object also varies, although they may agree quite satisfactorily on non-fluorescent objects.

The effective FWA concentration level in an object has been measured using highly sophisticated techniques. In one such technique, a standard object having a known FWA concentration is first illuminated by a source and the intensity of the light received from the object is measured. The object is then reilluminated after a filter which eliminates the light in the excitation band is placed over the source, and a second measurement is taken. The difference in these two measurements is directly related to the effective FWA concentration in the standard. The process is repeated for a sample of unknown FWA concentration and the two difference measurements are compared to determine the effective FWA concentration in the sample.

This technique is typically very cumbersome since it involves the mechnical movement of a filter in front of the source and is therefore relatively slow. Consequently, it is difficult to rapidly measure the FWA concentration which makes the technique less practical for many on line applications such as measuring the FWA concentration in paper as it emerges from the paper making process. Also since the paper has moved substantially between the two intervals of measurement, it cannot be assumed that the difference is solely a function of the FWA concentration. Any variation in a number of other attributes of the paper, such as opacity or whiteness, at the two points of measurement, could also affect the results.

SUMMARY OF THE INVENTION

It is an object of the present invention to provide an improved method and apparatus of determining the fluorescent properties of a sample.

It is a further object of the present invention to provide an improved method and apparatus for determining the color spectrum for a sample which contains fluorescent agents if illuminated by a defined source.

These and other objects and advantages are achieved in a color sensor which, in the illustrated embodiment of the present invention, has two light sources for illuminating an object or sample. One light source, such as an ultraviolet source, emits light primarily in the excitation range of the fluorescent agent in the object. In the illustrated embodiment, data is taken in two interleaved phases. In phase 1, both sources are on and in phase 2, the source emitting energy primarily in the excitation range is turned off while the other source remains on.

In the illustrated embodiment, a single measurement operation comprises accumulation of data in a relatively large number (>10) of each of the two phases. This is advantageous since the accumulated data in each phase to accurately represents the average product during the total measurement interval.

The sensor may be standardized by illuminating a standard of known fluorescent efficiency and known true reflectance (i.e., reflectance measured in the absence of fluorescent exciting radiation), to determine both the excitation energy of the ultraviolet source as well as the second source. Then, a sample of unknown FWA concentration may be illuminated by the sources and by comparing the data accumulated in each of the two phases during the measurement, the FWA concentration level can be determined. Furthermore, in another aspect of the present invention, the color spectrum of the sample if illuminated by an ideal CIE source or other defined source can be calculated.

BRIEF DESCRIPTION OF THE DRAWINGS

FIG. 8 is a schematic diagram of a driver circuit for the ultraviolet lamp of the color sensor of FIG. 4;

FIGS. 9(A,B) are timing diagrams illustrating the two phases of the data acquisition; and FIGS. 10(A-D) are additional timing diagrams for various waveforms of the driver circuit of FIG. 8.

DETAILED DESCRIPTION OF THE DRAWINGS

Figure 1:
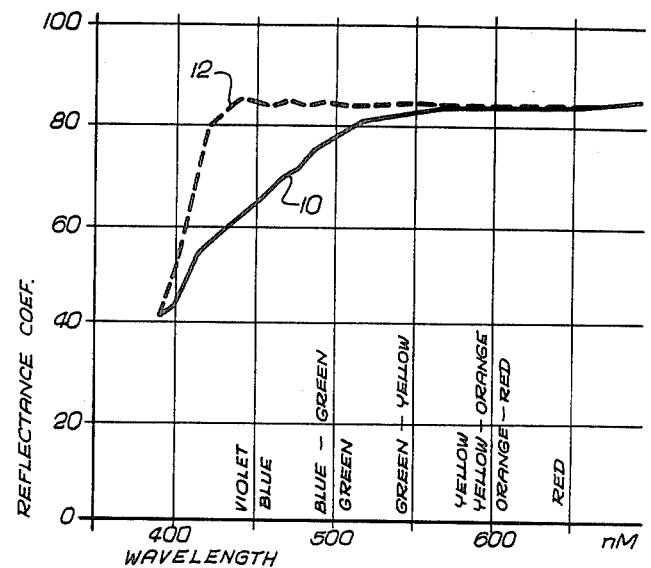
FIG. 1 is a graph showing two measured color spectra of light received from a particular paper sample in which fluorescence is suppressed in one instance and fluorescence is present in the other.

FIG. 1 shows two color spectra, indicated at 10 and 12, which show the distribution of light received from an object (here a sample of white paper) as a function of wavelength when illuminated by different types of sources. The first color spectrum 10 depicts the intensity or brightness of the light received from the sample for a range of wavelengths where fluorescence is absent or suppressed. The energy at each wavelength is expressed in terms of a reflectance co-efficient where 100 represents the reflection of a perfectly white object having no fluorescence.

As shown in FIG. 1, the color spectrum 10 drops off at the shorter wavelengths or higher energies which are at the blue-violet end of the spectrum. Because the yellow-red end of the spectrum is brighter, that is, more energy in the longer wavelengths is reflected by the sample than in the shorter wavelengths, the sample will appear beige or straw colored. In order to give the paper a whiter appearance, a fluorescent whitening agent (FWA) can be added to the paper during the paper making process to boost the blue wavelength energy received from the sample as represented by the color spectrum 12. Since the color spectrum 12 is relatively flat throughout the visible spectrum, the sample will have a white appearance.

Figure 2:
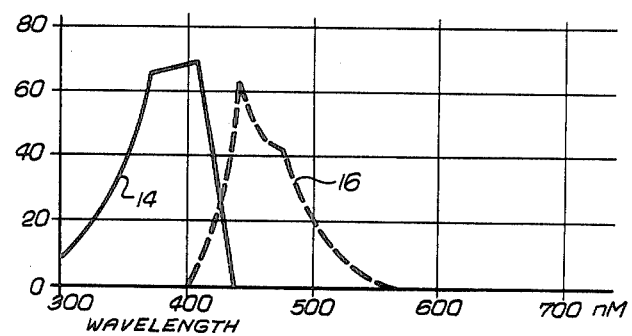
FIG. 2 is a graph illustrating the excitation and the emission spectra for a flourescent whitening agent.

As previously mentioned, the fluorescent whitening agents absorb light from the source which is in their excitation band and re-emit the light in a lower energy (longer wavelength) emission band. As shown in FIG. 2, the excitation band for a typical fluorescent whitening agent is in the violet and ultraviolet range and the emission band is primarily in the blue range. Consequently, the degree to which a paper is made to appear bluer (and therefore whiter) by the FWA depends upon the balance of energy in the violet and ultraviolet regions (less than 430 nm) of the source as compared to the blue regions, as well as the effective FWA concentration.

Figure 3:
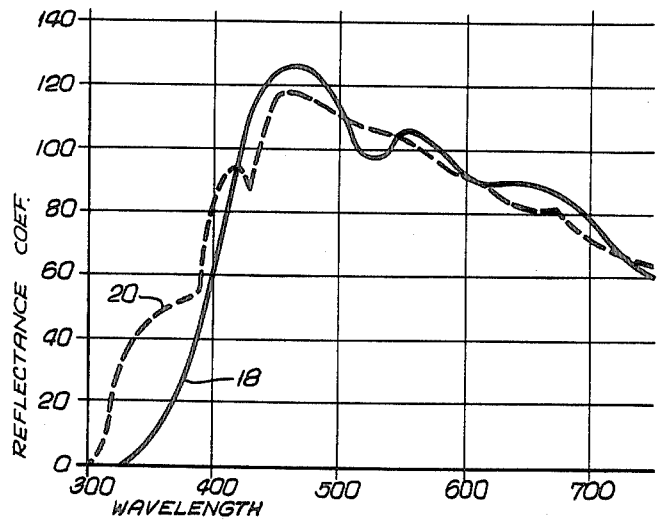
FIG. 3 illustrates the respective spectra for two CIE defined sources.

The distribution of energy in terms of wavelength for two different CIE defined sources is illustrated in FIG. 3. The distribution indicated at 18 is for the CIE standard source designated "C". The second distribution 20, for the CIE source "D65", indicates that the D65 source is brighter in the 300-400 nanometer range whereas the source C is brighter in the 400 to 500 nanometer range. Consequently, a paper sample with FWA is likely to appear bluer if illuminated by the source D65 as compared to the source C. However, the sources D65 and C as defined in FIG. 3 like most sources are extremely difficult to accurately duplicate. Thus, even if two color sensors both utlize "D65" sources, the sensors are likely to yield somewhat different color spectra for a single sample containing FWA.

Figure 4:
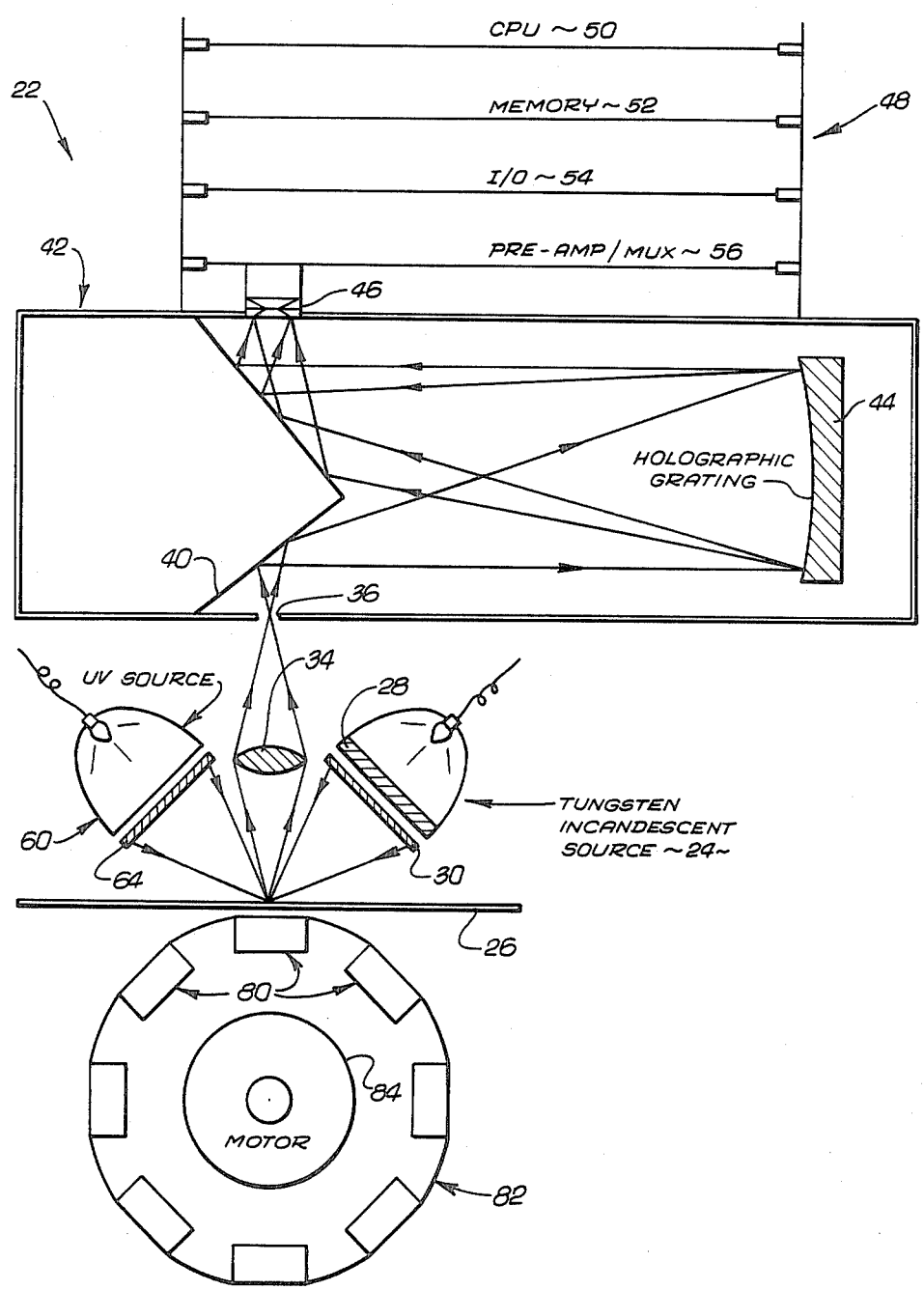
FIG. 4 is a schematic diagram of a color sensor in accordance with a preferred embodiment of the present invention.

Referring now to FIG. 4, a color sensor in accordance with a preferred embodiment of the present invention is indicated generally at 22. The color sensor 22 has a first source 24 of light which is used to illuminate the object to be tested, which in the illustrated embodiment is a sheet 26 of paper. The source 24 has a heat filter 28 to block infrared radiation and a color correcting filter 30 to redistribute the wavelengths at which the light is emitted.

The light source 24 is, in the illustrated embodiment, an incandescent tungsten lamp (modified by the color correcting filter so that its emission spectrum roughly approximates CIE illuminate "C") which therefore emits a significant amount of light in the ultraviolet or excitation range of fluorescent whitening agents. Accordingly, the paper 26 both reflects light from the source 24 and re-emits light absorbed from the source 24 in the emission range of the FWA.

The light reflected and emitted by the paper 26 is focused by a lens 34 through an aperture or slit 36 onto a folding mirror 40 of a wavelength dispersing assembly 42. The folding mirror 40 reflects the energy from the lens 34 onto a holographic grating 44 which disperses the energy by wavelength into a spectrum much like a rainbow and reflects the light back to the folding mirror 40A. The spectrum is reflected by the folding mirror 40A onto an array 46 of 32 diodes, each of which generates an electrical signal proportional to the total energy in the range of wavelengths which is directed to that particular diode.

The electrical output of each diode of the diode array 46 is sensed by a preamplifier and read by a computer 48 (as shown in the illustrated embodiment). The computer 48 includes a central processing unit or CPU 50, a memory 52, input/output (I/0) 54 and preamplifiers and multiplexers 56 for reading and processing the data from the diode array 46. The above-described elements 24-56 are well known to those skilled in the art and need not be described in greater detail.

In accordance with the present invention, the color sensor 22 has a second source 60 which emits light primarily in the excitation band of the fluorescent whitening agent. The second source 60 is an ultraviolet lamp in the illustrated embodiment, has a band pass filter 64, which transmits energy substantially in the excitation band of the FWA only. The second source 60 is rapidly turned on and off while the first source 24 remains on. As will be more fully discussed below, data is obtained while the second source 60 is on and also while the second source 60 is off. Differences in the two sets of data are used to compute the fluorescent whitening agent efficiency, or effective FWA concentration. Furthermore, a corrected color spectrum can be determined which would be obtained if the sample were illuminated by a defined source.

To calibrate the diodes of the diode array 46, the color sensor 22 has a plurality of standards 80 which are carried on a wheel 82. The standards include a very white sample which is moved in position by a stepper motor 84 to calibrate the sensor. Sensor calibration techniques are well known in the art.

Figure 5:
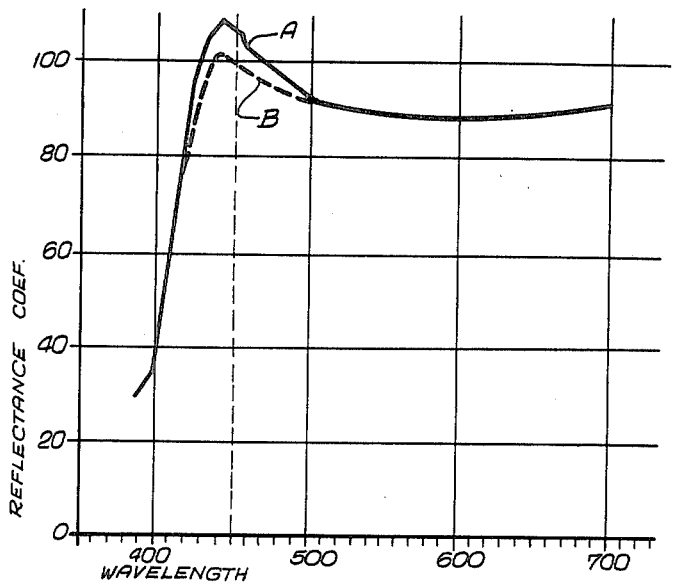
FIG. 5 illustrates two color spectra of a paper sample containing fluorescent whitening agent in which data has been taken (1) with the ultraviolet lamp of FIG. 4 on, and (2) with the ultraviolet lamp off.

After the sensor 22 has been calibrated, it is used to read a fluorescent standard sample with known fluorescent properties in order to determine the excitation energy in the ultraviolet source 60 as well as in the incandescent source 24. FIG. 5 shows an example of two color spectra which were obtained by the color sensor 22 when reading a sample with a high effective FWA concentration.

One diode of the diode array 46 is positioned to measure the energy of the light received from the sample at the 390 nanometer wavelength and another diode is positioned to measure the energy at the 700 nanometer wavelength, with the remaining 30 diodes being positioned to measure the energy at the wavelengths inbetween at 10 nanometer increments. The sensor produces the first spectrum A using both the UV source 60 and the incandescent source 24. In the illustrated embodiment, the outputs from the diode array 46 are read several times by the computer 48 to obtain an accumulated set of 32 data points during phase 1 in which both sources remain on.

In phase 2, the UV source 60 is turned off (while the incandescent source 24 remains on), and the output of the diode array 46 is again read several times to produce an accumulated phase 2 spectrum. As previously mentioned, the UV source 60 is cyclicly turned on and off, with the results of each cycle added to the previous accumulation. After a preset measurement interval, the computer stops data acquisition. An average intensity for each diode in phase 1 is then computed and stored in the computer as spectrum A for the fluorescent standard sample over the 390–700 nanometer range. Similarly, the intensity measurements from each diode of the diode array 46 while the UV source was off (phase 2) are averaged and stored by the computer producing the second spectrum B representing the energy of the light received from the standard sample when only the incandescent source 24 is on.

Figure 6:
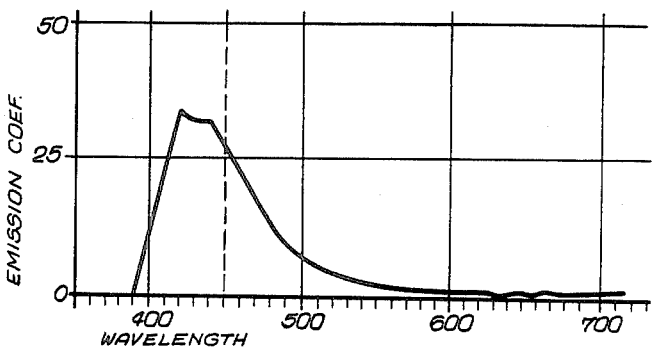
FIG. 6 is a graph showing the difference spectrum of the data illustrated in FIG. 5.

As shown in FIG. 5, the light from the standard sample is brighter at the bluish end of the spectra when the UV source 60 is on. The scaled difference between the two color spectra A and B plotted in FIG. 6 is stored in the computer. The increased brightness of the A spectrum is a result of the additional blue light emitted by the fluorescent whitening agent. The difference between the two color spectra A and B can be represented below as:

$$A_\lambda - B_\lambda = X_u \cdot F_{s\lambda} \qquad (1)$$

where $X_u$ is the excitation energy in the UV source 60 and $F_{s\lambda}$ represents the efficiency of the FWA standard to produce fluorescent emission at wavelength $\lambda$ when illuminated by a standard, fluorescence exciting source. Since the shape of the $F_{s\lambda}$ "spectrum" is fixed by the FWA dye emission curve, e.g., FIG. 2, it is sufficient to re-write equation (1) at a single wavelength:

$$A_\lambda - B_\lambda = X_u \cdot F_{s\lambda} \qquad (1)$$

where we define $F_s = F_{s\lambda p}$ and the wavelength is chosen to be the peak wavelength, $\lambda_p$. We henceforth call $F_s$ the 'fluorescent coefficient' of the standard.

As previously mentioned, the fluorescent coefficient $F_s$ of the fluorescent standard is known and equation (1) above may be rewritten as:

$$X_u = \frac{A_{\lambda p} - B_{\lambda p}}{F_s} \qquad (2)$$

whereby the excitation energy $X_u$ in the UV source 60 may be determined.

Equation (1) may also be rewritten as $$X_u = \left( \frac{A_\lambda - B_\lambda}{F_{s\lambda}} \right) \begin{matrix} \lambda_{max} \\ \lambda_{min} \end{matrix} \qquad (2')$$

where brackets denote an average of the quantity within over the wavelength range $\lambda$ min to $\lambda$ max. This average may reduce to measurement at a single wavelength $\lambda_p$ as shown in equation (2) above, or may cover the entire emission band, for example.

An additional quantity which is important to be determined is the excitation energy $X_s$ in the incandescent source 24 of the sensor 22. The quantity $X_s$ can be determined in accordance with the following relationship:

$$(B_{\lambda p} - C_{\lambda p}) = X_s \cdot F_s \qquad (3)$$

or $$X_s = \frac{B_{\lambda p} - C_{\lambda p}}{F_s} \qquad (4)$$

where the color spectrum C is the distribution of light which would be received from the standard sample if fluorescence was completely suppressed. In other words, the C spectrum shows the reflectance properties only of a sample, and is obtained for the standard sample using known laboratory techniques and equipment. The C spectrum for the standard sample is stored in the computer and is utilized after the B spectrum has been obtained to compute the excitation energy $X_s$ in the incandescent source 24. In this manner, the source values $X_u$ and $X_s$ are calculated and stored as part of a standardization routine in which a standard sample is first read.

After the color sensor 22 has been standardized as described above, the color sensor 22 is ready to measure a sample of unknown fluorescent coefficient (FWA concentration). FIG. 4 shows a sheet 26 of paper positioned to be read by the color sensor 22. The color sensor 22 may be used in a paper mill for example to measure the fluorescent properties and the color of paper as it is produced. Of course, the color sensor 22 is also suitable for color measurements of other objects and other fluorescent agents (FA).

Figure 7:
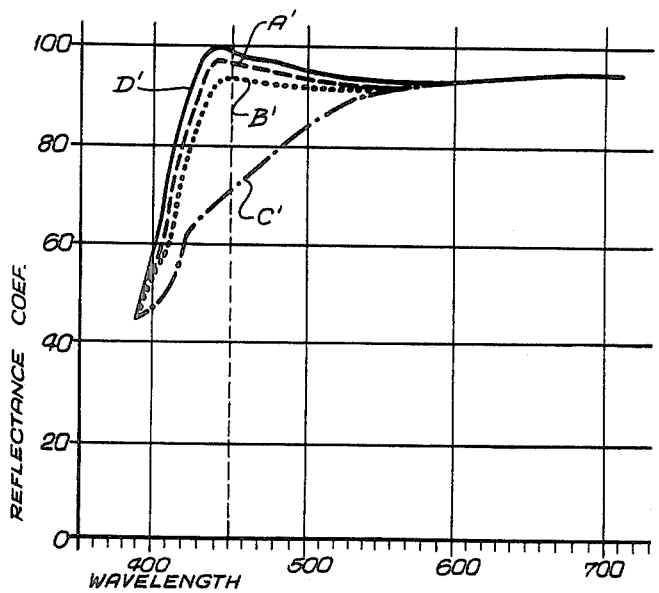
FIG. 7 shows four color spectra for a paper sample containing a fluorescent whitening agent, two spectra of which are measured and two spectra of which are calculated.

To read the sample 26, the incandescent source 24 again remains on while the UV source 60 is cyclicly modulated on and off. The intensities measured by the color sensor 22 at the 32 wavelength increments yield two color spectra designated A' and B' as shown in FIG. 7. As before, the color spectrum B' represents the measured relative intensities of the light received from the sample 26 when only the incandescent source 24 is on and the A' spectrum represents the measured relative intensities when the light from the UV source 60 is added to that of the incandescent source 24 to illuminate the sample 26. Since the excitation energy $X_u$ in the UV source 60 has been determined during the standardization routine, the fluorescent efficiency spectrum $F_\lambda'$ and the fluorescent coefficient, F' of the sample can be calculated by rearranging equations (1) and (2) as set forth below:

$$F_\lambda' = \frac{(A_\lambda' - B_\lambda')}{X_u} \quad (5)$$

$$F = \frac{(A_{\lambda p}' - B_{\lambda p}')}{X_u} \quad (5')$$

Having determined the fluorescent efficiency of the sample 26, the color spectrum C' which would be obtained for the sample 26 if fluorescence was totally suppressed can be calculated by rearranging equation (4) as:

$$C_\lambda' = B_\lambda' - (X_s \cdot F_\lambda') \quad (6)$$

where the excitation energy $X_s$ in the incandescent source 24 is determined during the standardization step.

In the illustrated embodiment, the source excitation energies $X_u$ and $X_s$ and the fluorescent coefficient F' are calculated using the measured values of the color spectra A' and B' at the 450 nanometer wavelength because this has been found to be at or near the peak in the emission for most common FWA dyes.

Having determined the fluorescent efficiency spectrum $F_\lambda'$ and the suppressed fluorescence color spectrum $C_\lambda'$ of the sample 26, a color spectrum D' which would be produced by the sample 26 if illuminated by an ideal CIE source can now be calculated where the excitation energy $X_D$ in the CIE defined standard source is known. Such a spectrum is indicated at D' in FIG. 7 and is calculated as set forth below:

$$(D_\lambda' - C_\lambda') = X_D \cdot F_\lambda' \quad (7) \text{ or}$$

$$D_\lambda' = C_\lambda' + (X_D \cdot F_\lambda') \quad (8)$$

It is seen that the spectrum $D_\lambda'$ is fully corrected to a true standard defined source. The $D_\lambda'$ spectrum can therefore be used for all subsequent calculations of color coordinates and whiteness or brightness for comparison purposes.

FIG. 8 shows a lamp driver circuit 100 for the UV source 60 of FIG. 4. The driver circuit 100 includes an oscillator 102 which outputs a 35 kilohertz clock signal to a pulse generator 104. The computer 48 of FIG. 4 outputs a 20 hertz "on/off" signal (depicted at (A) in FIG. 9) to the pulse generator 104, to control the on/off modulation of the source 60 at a 20 hertz rate as depicted at (B) in FIG. 9. Thus, the source 60 is on for 25 millisecond (ms) and off for 25 ms of each cycle.

During the 25 ms on period, the source 60 is actually pulsed in the illustrated embodiment to increase lamp life. Accordingly, during the 25 ms on period of the source 60, the pulse generator 104 generates two drive signals, X and Y, which are coupled to the gates of two FET transistor switches 106 and 108, respectively. The drive signals X and Y are depicted at (A) and (B) in FIG. 10 and each have a 30 microsecond period with a 3 microsecond pulse width which is set by an input 110 of the pulse generator 104. As shown in FIG. 10, the drive signals X and Y are 180° out of phase, and thus the switches 106 and 108 are closed 180° out of phase.

A transformer 112 having a primary coil 114 coupled to the switches 106 and 108 is energized by the alternate closing of the switches 106 and 108 by the drive signals X and Y, respectively. A secondary coil 116 of the transformer 112 produces an oscillating output voltage represented at (C) in FIG. 10, which is applied across the UV source 60 through a ballast resistor 118. The oscillating voltage across the source causes the source 60 to pulse once every 15 microseconds as indicated at (D) in FIG. 10. This rapid pulsing of the uv source 60 during the 25 ms on period of the source 60 is represented by the vertical lines of the waveform at (B) in FIG. 9. Because the preamplifiers 56 coupled to the outputs of the diode array 46 have a time constant of approximately $2\frac{1}{2}$ milliseconds, the UV source 60 is effectively on constantly with respect to the array 46 during the 25 millisecond on period.

After the UV source 60 is turned on at the start of each 25 millisecond on period, the computer 48 waits approximately 10 milliseconds before reading the 32 diodes to allow sufficient time for the preamplifiers to respond to the new lighting condition. The 32 diodes are read 3 or 4 times at 5 millisecond intervals to obtain 3 or 4 sets of data for the 32 diodes while both the UV source 60 and the incandescent source 24 are on. During the 25 millisecond off period, the sequence is repeated, waiting 10 milliseconds before taking 3 or 4 sets of data while only the incandescent source 24 is on.

This cycle of taking data while the UV source 60 is off for 25 ms and then while the UV source 60 is on for 25 ms is repeated for approximately a second to define a data measurement interval or segment. Data from each diode while the UV source 60 was off is averaged over the whole data segment to produce the data points plotted in the B spectrum previously described. Similarly, the data for each diode taken while the UV source 60 was on is averaged over the whole data segment to produce the A spectrum. The rapid interleaving of data reads under the two lighting conditions reduces the effect of noise in the electronics and substantially eliminates the effect that slow drifts in electronics or optical efficiency or variation in the measured paper would otherwise have on the difference spectrum and hence the measurement of the fluorescent coefficient.

It is seen from the above that the present invention provides an improved color sensor which can calculate the fluorescent coefficient, related to the effective FWA concentration of a sample without the use of moving filters and the like. Moreover, the color sensor can generate a spectrum which is corrected to show the spectrum of the sample as it would be if illuminated by a defined source such as a CIE source, or other lighting sources in which the excitation energy is known. Consequently, the color of a particular sample can be predicted for a variety of lighting conditions.

It will, of course, be understood that modifications of the present invention, in its various aspects, will be apparent to those skilled in the art, some being apparent only after study, others being merely matters of routine electronic and mechanical design. For example, light detectors other than diodes may be utilized and other types of light sources may also be used. Other embodiments are also possible, with their specific designs dependent upon the particular application. As such, the scope of the invention should not be limited by the particular embodiment herein described, but should be defined only by the appended claims and equivalents thereof.

I claim:

1. In a color sensor of the type having at least one light detector for detecting the light reflected or emitted by a sample containing a fluorescent agent (FA), the improvement comprising:

a first source of light positioned to illuminate the sample;

a second source of light positioned to illuminate the sample wherein at least a portion of the light emitted by the second source is in the excitation band of the FA;

means for modulating the intensity of the second source independently of the first in a plurality of first and second phases wherein in each first phase the sample is illuminated by both the first and second sources and in each second phase any level of illumination of the sample by the second source differs from the level of illumination provided by the second source in the first phases; and means for measuring the energy received from the object in phase synchronism with the independent modulation of the second source.

2. An apparatus for measuring the fluorescent properties of an object comprising:

a first light source for illuminating the object;

a second light source for illuminating the object wherein the second source emits a predetermined intensity of light in the excitation range of the object;

means for alternately turning the second source on and off while the first source is on;

means for sensing the light received from the object in a first period in which the first source is on and the second source is off and in a second period in which both the first and second sources are on;

means for computing the fluorescence based on the difference in light sensed during the two periods and on the predetermined intensity of the light of the second source.

3. A method of measuring the effective fluorescence of an object containing a fluorescent agent (FA), comprising the steps of:

illuminating the object with a first source of light;

sensing the intensity of the light received from the object at one or more wavelengths while the object is illuminated by the first source to provide a first intensity measurement;

illuminating the object with a second source of light while the first source also illuminates the object, said second source emitting a predetermined intensity of energy in the excitation range of the FA;

sensing the intensity of the light received from the object while the object is illuminated by both sources to provide a second intensity measurement; and determining the effective fluorescence of the object from the difference in the two intensity measurements and said predetermined excitation intensity of the second source.

4. A method of determining the effective spectrum of a fluorescent object as if illuminated by a defined source, comprising the steps of:

illuminating the object at a first known level of fluorescent excitation energy;

sensing the intensity of the light received from the object at a plurality of wavelengths while the object is illuminated with the first level of intensity to provide a first spectrum measurement;

illuminating the object with fluorescent excitation energy of a second level of intensity which is different from the first level by a known amount;

sensing the intensity of the energy received from the object at said plurality of wavelengths while the object is illuminated by energy of the second level to provide a second color spectrum measurement;

determining the fluorescent coefficient of the object from the difference in the two spectra measurements and the difference in the fluorescent excitation energy;

determining the fluorescence suppressed spectrum of the object from the first known level of excitation energy and the determined fluorescent coefficient; and determining the correct color spectrum of the object as if it had been illuminated by a defined source from the determined fluorescent coefficient and the defined level of excitation energy of the defined source and the determined fluorescence suppressed spectrum.

5. A method of measuring the fluorescent efficiency spectrum F' in an unknown sample, comprising the steps of:

(a) illuminating a standard sample of known fluorescent coefficient $F_s$ with a first level $X_s$ of excitation energy from a first source and detecting the level $B_\lambda$ of energy received from the sample at one or more wavelengths;

(b) illuminating the standard sample with a second source having a level $X_u$ of excitation energy and determining the intensity $A_\lambda$ of energy received from the sample at said one or more wavelengths;

(c) computing the level $X_u$ of excitation energy from the second source as follows:

$$X_u = \left( \frac{A_\lambda - B_\lambda}{F_s} \right) \begin{matrix} \lambda_{max} \\ \lambda_{min} \end{matrix}$$

(d) illuminating a sample of unknown fluorescence with said first level of illumination and determining the intensity $B_\lambda'$ of light received from the sample;

(e) illuminating the unknown sample with both said first and second sources of illumination energy and determining the level $A_\lambda'$ of energy received from the sample; and computing the fluorescence efficiency spectrum $F_\lambda'$ in the unknown sample as follows:

$$F_\lambda' = \frac{(A_\lambda' - B_\lambda')}{X_u}.$$

6. In a color sensor of a type having at least one detector for detecting light energy reflected or emitted by a sample containing a fluorescent agent (FA), the improvement comprising:

a first source of light energy positioned to illuminate the sample;

a second source of light energy positioned to illuminate the sample wherein at least a portion of the light energy emitted by the second source is in the excitation band of the FA;

means for alternately turning one source on and off while the other source remains on; and means for reading the energy detector while both sources are on, and also while one source is on and the other source is off.

7. A method of computing a corrected spectrum of light energy received from a sample containing a fluorescent agent (FA) as if it had been illuminated by a defined source, comprising the steps of:

(a) illuminating a standard sample of known fluorescent efficiency $F_{s\lambda}$ with a first level of illumination and detecting a first spectrum $B_\lambda$ of light energy received from the sample at a plurality of wavelengths $\lambda$;

(b) illuminating the standard sample with a second level of illumination and detecting a second spectrum $A_\lambda$ of light energy received from the sample at said plurality of wavelengths;

(c) computing the level $X_u$ of increased excitation energy between the two levels as follows:

$$X_u = \left(\frac{A_\lambda - B_\lambda}{F_{s\lambda}}\right) \frac{\lambda_{max}}{\lambda_{min}};$$

(d) computing the level $X_s$ of excitation energy of said first level of illumination as follows:

$$X_s = \left(\frac{B_\lambda - C_\lambda}{F_{s\lambda}}\right) \frac{\lambda_{max}}{\lambda_{min}};$$

where the suppressed fluorescent spectrum $C_\lambda$ of the standard sample is known; and (e) illuminating a sample of unknown fluorescence with said first level of energy and detecting a spectrum $B_\lambda$ of light energy received from the sample at said plurality of wavelengths;

(f) illuminating the unknown sample with said second level of energy and detecting a spectrum $A_\lambda'$ of light energy received from the sample at said plurality of wavelengths;

(g) computing the fluorescent efficiency $F_\lambda'$ in the unknown sample as follows:

$$F_\lambda' = \frac{(A_\lambda' - B_\lambda')}{X_u}$$

(h) computing the fluorescent suppressed spectrum $C'$ of the unknown sample as follows:

$$C_\lambda' = B_\lambda' - (X_s F_\lambda');$$

(i) computing the corrected spectrum $D_\lambda'$ of the unknown sample as if it had been illuminated by a defined source as follows:

$$PI\ D_\lambda' = C_\lambda' - (X_D F_\lambda');$$

where the level $X_D$ of excitation energy of the defined source is known.

8. In a color sensor of a type having at least one light detector for detecting light reflected or emitted by a sample containing a fluorescent agent (FA), the improvement comprising:

a first source of light energy positioned to illuminate the sample;

a second source of light energy positioned to illuminate the sample wherein at least a portion of the light emitted by the second source is in the excitation band of the FA;

means for modulating the intensity of the second source which contains at least a portion of its energy in the excitation band of the FA; and means for measuring at one or more wavelengths both the average intensity and the amplitude of modulation of the energy received from the object.

9. A method of computing a corrected spectrum of light energy received from a sample containing a fluorescent agent (FA) if illuminated by a defined source, comprising the steps of:

(a) illuminating a standard sample with a first level of illumination $X_s$ and detecting a first spectrum of light energy received from the sample at at least one wavelength;

(b) illuminating the standard sample with a second level of illumination and detecting a second spectrum of light received from the sample at said wavelength;

(c) computing the level $X_u$ of increased excitation energy between the two levels based on the detected first and second spectra;

(d) illuminating a sample of unknown fluorescence with said first level of energy and detecting a spectrum $B_\lambda'$ of light energy received from the sample at a plurality of wavelengths;

(e) illuminating the unknown sample with said second level of energy and detecting a spectrum $A_\lambda'$ of light energy received from the sample at said plurality of wavelengths;

(f) computing the fluorescent efficiency $F_\lambda'$ in the unknown sample as follows:

$$F_\lambda' = \frac{(A_\lambda' - B_\lambda')}{X_u}$$

(g) computing the fluorescent suppressed spectrum $C_\lambda'$ of the known sample as follows:

$$C_\lambda' = B_\lambda' - (X_s F_\lambda');$$

(h) computing the corrected spectrum $D_\lambda'$ of the unknown sample as if it had been illuminated by a defined source as follows:

$$D_\lambda' = C_\lambda' - (X_D F_\lambda');$$

where the level $X_D$ of excitation energy of the defined source is known.

10. A method of sensing the fluorescent properties of a sample containing fluorescent agents comprising the steps of:

illuminating with a first light source said sample with light of a first spectrum; simultaneously to illuminating with a second light source said sample with light of a second spectrum, which second spectrum overlaps the excitation spectral range of said fluorescent agents to a greater degree than said first spectrum; simultaneously to modulating the intensity of said illumination by the second light source relative to the intensity of said illumination by the first light source; simultaneously to detecting in a sensor the energy received from said sample resultant from said illuminations; and calculating in electronic circuitry from said detected energy received in respect of said modulation, the fluorescent properties of said sample.

11. The method according to claim 10 wherein said first spectral range of the first light source is outside said excitation spectral range of said fluorescent agents.

12. The method of claim 10 further comprising the step of determining the color spectrum of said sample, wherein said step of illuminating with a first light source further comprises:
   illuminating with a first light source of a defined spectrum; and wherein said step of illuminating with a second light source further comprises:
   illuminating with a second light source of a defined spectrum; and wherein said step of detecting further comprises:
   detecting in a sensor the energies received from said sample, resultant from said illuminatings, at a plurality of spectral frequencies; and wherein said step of calculating further comprises:
   calculating from said detected energies the color spectrum of said sample.

13. The method according to claim 10 wherein said first light source is a tungsten lamp; and wherein said second light source is an ultraviolet lamp.

14. An apparatus for sensing the fluorescent properties of a sample containing fluorescent agents having an excitation spectral range, comprising:
   first light source means for illuminating said sample with light of a first spectrum substantially overlapping the excitation spectral range of said fluorescent agents;
   second light source means for, simultaneously to the illumination by said first light source means, illuminating said sample with light of a second spectrum, which second spectrum is less overlapping of the excitation spectral range of said fluorescent agents than is said first spectrum;
   modulation means for modulating the illumination intensity of said first light source means relative to the illumination intensity of second light source means;
   sensor means for detecting the energy levels received from said sample resultant from said illuminations by said first and second light source means;
   calculating means for calculating, from the difference in said detected energy levels restlting from said modulation, the fluorescent properties of said sample.

15. The apparatus according to claim 14 wherein said second spectrum does not overlap the excitation spectral range of said fluorescent agents.

16. The apparatus of claim 14 further for determining the color spectrum of said sample wherein the first spectrum of said first light source means is a defined spectrum; and wherein said second spectrum of said second light source means is a defined spectrum; and wherein said sensor means further has means for detecting energy levels at a plurality of spectral points within said first spectrum and said second spectrum; and wherein said calculating means further has means for calculating, from the differences in the detected energy levels at said spectral point resulting from said modulation, the color spectrum of said sample.

* * * * *